United States Patent [19]

Stahly

[11] Patent Number: 4,675,448
[45] Date of Patent: Jun. 23, 1987

[54] CHLORINATION PROCESS

[75] Inventor: Barbara C. Stahly, Baton Rouge, La.

[73] Assignee: Ethyl Corporation, Richmond, Va.

[21] Appl. No.: 848,969

[22] Filed: Apr. 7, 1986

Related U.S. Application Data

[63] Continuation-in-part of Ser. No. 701,293, Feb. 13, 1985, abandoned.

[51] Int. Cl.$^4$ .............................................. C07C 45/63
[52] U.S. Cl. .................................. 568/315; 568/316
[58] Field of Search ................................ 568/315, 316

[56] References Cited

U.S. PATENT DOCUMENTS

| | | | |
|---|---|---|---|
| 3,367,857 | 2/1968 | Falbe et al. | 568/316 |
| 3,390,187 | 6/1968 | Falbe et al. | 568/316 |
| 3,850,989 | 11/1974 | Havinga et al. | 568/316 |
| 4,001,335 | 1/1977 | Schaffner et al. | 568/316 |
| 4,289,909 | 9/1981 | Freenor et al. | 568/315 |

FOREIGN PATENT DOCUMENTS

| | | | |
|---|---|---|---|
| 2045760A | 11/1980 | United Kingdom | 546/233 |
| 2097000A | 10/1982 | United Kingdom | 546/233 |

OTHER PUBLICATIONS

Minakov et al., *Chemical Abstracts*, vol. 87, 6756z (1977).

*Primary Examiner*—James H. Reamer
*Attorney, Agent, or Firm*—Donald L. Johnson; John F. Sieberth; Patricia J. Hogan

[57] ABSTRACT

1-[2,5-Bis(2,2,2-trifluoroethoxy)phenyl]ethanone is chlorinated to 1-[2,5-bis(2,2,2-trifluoroethoxy)phenyl]-2,2-dichloroethanone and, if desired, to 1-[2,5-bis(2,2,2-trifluoroethoxy)phenyl]-2,2,2-trichloroethanone in a solvent mixture of about 0.5–35 parts by volume of 1,2-dichloroethane and one part by volume of acetic acid. The products can then be converted to flecainide. In a preferred embodiment of the invention, the starting material is a crude, wet material that is prepared with a minimum of solids handling.

11 Claims, No Drawings

CHLORINATION PROCESS

CROSS-REFERENCE TO RELATED APPLICATION

This application is a continuation-in-part of copending application Ser. No. 701,293, filed Feb. 13, 1985 now abandoned.

FIELD OF INVENTION

This invention relates to flecainide and more particularly to a chlorination process useful in its preparation.

Glossary

For convenience, various compounds mentioned in this specification are sometimes designated herein by the following abbreviations:
Flecainide: N-(2-piperidinylmethyl)-2,5-bis(2,2,2-trifluoroethoxy)benzamide,
BTB: 1,4-bis(2,2,2-trifluoroethoxy)benzene,
BTA: 1-[2,5-bis(2,2,2-trifluoroethoxy)phenyl]ethanone,
$Cl_2BTA$: 1-[2,5-bis(2,2,2-trifluoroethoxy)phenyl]-2,2-dichloroethanone,
$Cl_3BTA$: 1-[2,5-bis(2,2,2-trifluoroethoxy)phenyl]-2,2,2-trichloroethanone,
DMF: N,N-dimethylformamide,
EDC: 1,2-dichloroethane.

Background

As disclosed in British Patent Application GB No. 2 045 760 A (Leir), it is known that flecainide is an antiarrhythmic that can be prepared by (1) reacting 1,4-dibromobenzene with 2,2,2-trifluoroethanol in the presence of cupric bromide, sodium hydride, and DMF, (2) isolating the resultant BTB and acetylating it in the presence of a Lewis acid and a suitable solvent, such as EDC, (3) isolating the resultant BTA and chlorinating it to $CL_2$ BTA in a suitable solvent, such as acetic acid or a chlorinated hydrocarbon, (4) adding a buffering agent, such as sodium acetate, and continuing chlorination to form $Cl_3BTA$, and (5) isolating the chlorinated product and converting it to flecainide by reaction with 2-(aminomethyl)piperidine or by reaction with 2-(aminomethyl)pyridine followed by reduction.

Leir's process has decided advantages but also has disadvantages. The use of his preferred acetic acid solvent in the chlorination step can lead to the formation of as much as 25 area percent of ring-chlorinated by-products in some instances, and the substitution of one of his chlorinated hydrocarbons, such as EDC, for his acetic acid makes the reaction too slow for a commercial operation. His isolation of the majority of his intermediates is also commercially unattractive in that it necessitates too much handling of solids.

Summary of Invention

An object of this invention is to provide a novel process for preparing $Cl_2BTA$.

Another object is to provide a novel process for preparing $Cl_3BTA$.

Still another object is to provide a novel process for preparing flecainide.

A further object is to provide such processes that are efficient and commercially attractive.

These and other objects are attained by chlorinating BTA in a solvent mixture of EDC and acetic acid in a volume ratio of about 0.5-35/1 so as to form $Cl_2BTA$ and, when appropriate, converting the $Cl_2BTA$ to a desired derivative, such as $Cl_3BTA$ or flecainide.

Detailed Description

In the broadest aspect of the invention, the BTA that is subjected to chlorination may be a 1-[2,5-bis(2,2,2-trifluoroethoxy)phenyl]ethanone that is prepared by any suitable means, e.g., any of the relevant processes of Leir, the teachings of which are incorporated herein by reference. However, it has unexpectedly been found that neither the BTA nor the BTB employed in its synthesis has to be isolated in substantially pure solid form, as in the Leir processes, to be useful in the present invention. In fact, when it is desired to synthesize $Cl_2BTA$ or a derivative by a process that involves a minimum of solids handling, the BTA is preferably prepared by a technique wherein solvent extraction is employed instead of Leir's filtrations to recover the BTA product and the BTB intermediate.

In a particularly preferred embodiment of the invention, the BTA is a crude reaction product prepared by (1) reacting 1,4-dibromobenzene with 2,2,2-trifluoroethanol in the presence of cupric bromide, sodium hydride, and DMF to form a reaction mixture containing BTB, (2) extracting the reaction mixture with EDC to form a crude BTB extract, (3) washing the extract to remove DMF, and (4) acetylating the crude BTB in the presence of a Lewis acid and EDC and acidifying and washing the resultant reaction mixture to provide an organic phase comprising a crude, wet BTA.

To the extent that steps of this preferred process are taught by Leir, it is frequently desirable to employ his techniques in conducting the reactions; and, to the extent that they are not taught by Leir, other conventional techniques may be employed. It is generally preferred to conduct the BTB synthesis as taught by Leir, using reaction temperatures up to reflux temperatures, extract the reaction mixture with EDC, wash the extract with dilute aqueous acid, and then acetylate the crude BTB in essentially the same way as Leir acetylates his isolated BTB. In the acetylation step it is generally preferred to employ acetyl chloride or acetic anhydride as the acetylating agent, use aluminum chloride as the Lewis acid catalyst, and conduct the reaction under mild conditions, e.g., about 5°-15° C. Then the product is acidified and washed as in Leir but, unlike the product of Leir, is left in EDC solution instead of being isolated in substantially pure solid form.

In the chlorination process of the invention, BTA is chlorinated in a solvent mixture of EDC and acetic acid in a volume ratio of about 0.5-35/1, preferably at a temperature of about 50°-60° C. The use of this solvent system dramatically reduces the formation of the ring-chlorinated side products that may be produced when acetic acid is employed as the sole solvent, and it requires less time for the reaction than the use of either EDC or acetic acid as the sole solvent. Optimum results are obtained with a solvent mixture of about 1-20, preferably about 2-20, parts by volume of EDC per part by volume of acetic acid.

The aforementioned chlorination process results in the formation of $Cl_2BTA$ together with some $Cl_3BTA$. When complete conversion to $Cl_3BTA$ is desired, a second chlorination step is conducted as in Leir to accomplish this conversion. As in Leir, a buffering agent such as sodium acetate is added to the reaction mixture, and the temperature is suitably raised to about 80°-100°

C., preferably reflux temperature, while continuing the chlorination.

When desired, the Cl₃BTA produced by the two-step chlorination may be converted to flecainide by the techniques of Leir, i.e., by reacting it with 2-(aminomethyl)-piperidine or by reacting it with 2-(aminomethyl)pyridine and then reducing the product.

The invention is particularly advantageous as an efficient, commercially attractive method of preparing Cl₂BTA, Cl₃BTA, and flecainide in high yields with a minimum of solids handling.

The following examples are given to illustrate the invention and are not intended as a limitation thereof.

EXAMPLE I

A solution of 7.9 mmols of BTA in 5 ml of EDC was treated with 2 ml of glacial acetic acid and heated to 50° C. Chlorine was bubbled into the solution while keeping the temperature at 50°–55° C. until thin layer chromatography (tlc) indicated complete disappearance of the starting material. Then 1.5 g of anhydrous sodium acetate was added and chlorine addition was continued until GC analysis showed less than 3% of the intermediate Cl₂BTA remaining. The reaction mixture was poured into a cooled solution of 0.3 g of sodium bisulfite and 15 ml of water. The aqueous phase was washed with 5 ml of EDC. Combined organic layers were washed with 2×10 ml portions of water, dried over magnesium sulfate, and evaporated to provide an 85% yield of Cl₃BTA.

EXAMPLE II

Part A

A 27.5 g sample of BTB prepared by the procedure of Leir in his Example 2, paragraph 2, was dissolved in 115 mL of EDC and dried with magnesium sulfate to form a solution containing 72.7 mmols of BTB. This solution was cooled to 5° C. and treated with 95.5 mmols of aluminum chloride while keeping the temperature under 15° C. The mixture was then cooled to 5° C., treated with 93 mmols of acetyl chloride while keeping the temperature under 10° C., stirred at 5° C. for 4 hours, and poured into a 20° C. solution of 60 mL of water and 7.8 g of concentrated HCl, keeping the temperature under 50° C. The aqueous phase was washed with 50 mL of EDC. The combined organic phases were washed with two 15 mL portions of water. GC analysis of the final product solution showed a 90% yield of BTA.

Part B

A portion of the crude, undried BTA extract of Part A (63.8 mmols of BTA in 165 mL of EDC) was treated with 22 mL of glacial acetic acid and heated to 50° C. Chlorine was bubbled into the solution keeping the temperature at 50°–55° C. until tlc showed no BTA remaining. The reaction mixture was purged with nitrogen, treated with 33.0 g of anhydrous sodium acetate, and heated to reflux (80°–85° C.). Chlorine addition was continued until only Cl₃BTA was present by tlc. GC analysis showed 90 area percent Cl₃BTA.

EXAMPLE III

A procedure similar to that of Example I was used to chlorinate BTA in a mixture of 20 parts by volume of EDC and one part by volume of acetic acid. GC analysis of the product solution showed 70 area percent Cl₃BTA.

It is obvious that many variations can be made in the products and processes set forth above without departing from the spirit and scope of this invention.

I claim:

1. A process which comprises chlorinating 1-[2,5-bis(2,2,2-trifluoroethoxy)phenyl]ethanone in a solvent mixture of about 0.5–35 parts by volume of 1,2-dichloroethane and one part by volume of acetic acid so as to form 1-[2,5-bis-2,2,2-trifluoroethoxy)phenyl]-2,2-dichloroethanone.

2. The process of claim 1 wherein the solvent is a mixture of about 1–20 parts by volume of 1,2-dichloroethane and one part by volume of acetic acid.

3. The process of claim 2 wherein the 1,2-dichloroethane/acetic acid volume ratio is about 2–20/1.

4. The process of claim 1 wherein the chlorination is conducted at about 50°–60° C.

5. The process of claim 1 wherein the 1-[2,5-bis(2,2,2-trifluoroethoxy)phenyl]ethanone that is subjected to chlorination is the crude reaction product obtained by (1) reacting 1,4-dibromobenzene with 2,2,2-trifluoroethanol in the presence of cupric bromide, sodium hydride, and N,N-dimethylformamide to form a reaction mixture containing 1,4-bis(2,2,2-trifluoroethoxy)benzene, (2) extracting the reaction mixture with 1,2-dichloroethane to form a crude 1,4-bis(2,2,2-trifluoroethoxy)benzene extract, (3) washing the extract to remove N,N-dimethylformamide, and (4) acetylating the crude 1,4-bis(2,2,2-trifluoroethoxy)benzene in the presence of a Lewis acid and 1,2-dichloroethane and acidifying and washing the resultant reaction mixture to provide an organic phase comprising a crude, wet 1-[2,5-bis(2,2,2-trifluoroethoxy)phenyl]ethanone.

6. The process of claim 1 wherein the 1-[2,5-bis(2,2,2-trifluoroethoxy)phenyl]ethanone is chlorinated to 1-[2,5-bis(2,2,2-trifluoroethoxy)phenyl]-2,2-dichloroethanone in the solvent mixture, a buffering agent is added, and chlorination is continued so as to form 1-[2,5-bis(2,2,2-trifuoroethoxy)phenyl]-2,2,2-trichloroethanone.

7. The process of claim 6 wherein the buffering agent is sodium acetate.

8. In a process for preparing 1-[2,5-bis(2,2,2-trifluoroethoxy)phenyl]-2,2,2-trichloroethanone by chlorinating 1-[2,5-bis(2,2,2-trifluoroethoxy)phenyl]ethanone to 1-[2,5-bis(2,2,2-trifluoroethoxy)phenyl]-2,2-dichloroethanone in the presence of a solvent, adding a buffering agent, and continuing chlorination, the improvement which comprises employing a crude, wet 1-[2,5-bis(2,2,2-trifluoroethoxy)phenyl]ethanone as the starting material and conducting the chlorination in a solvent mixture of about 0.5–35 parts by volume of 1,2-dichloroethane and one part by volume of acetic acid.

9. The process of claim 8 wherein the crude, wet 1-[2,5-bis(2,2,2-trifluoroethoxy)phenyl]ethanone is the product obtained by (1) reacting 1,4-dibromobenzene with 2,2,2-trifluoroethanol in the presence of cupric bromide, sodium hydride, and N,N-dimethylformamide to form a reaction mixture containing 1,4-bis(2,2,2-trifluoroethoxy)benzene, (2) extracting the reaction mixture with 1,2-dichloroethane to form a crude 1,4-bis(2,2,2-trifluoroethoxy)benzene extract, (3) washing the extract to remove N,N-dimethylformamide, and (4) acetylating the crude 1,4-bis(2,2,2-trifluoroethoxy)benzene in the presence of a Lewis acid and 1,2-dichloroethane and acidifying and washing the resultant reaction mixture to provide an organic phase comprising a crude, wet 1-[2,5-bis(2,2,2-trifuoroethoxy)phenyl]ethanone.

10. In a process for preparing flecainide by (1) chlorinating 1-[2,5-bis(2,2,2-trifluoroethoxy)phenyl]ethanone to 1-[2,5-bis(2,2,2-trifluoroethoxy)phenyl]-2,2-dichloroethanone in the presence of a solvent, adding a buffering agent, and continuing chlorination so as to form 1-[2,5-bis(2,2,2-trifluoroethoxy)phenyl]-2,2,2-trichloroethanone and (2) converting the resultant product to flecainide by (a) reaction with 2-(aminomethy)piperidine or (b) reaction with 2-(aminomethyl)pyridine followed by reduction, the improvement which comprises conducting the chlorination in the presence of a solvent mixture of 0.5–35 parts by volume of 1,2-dichloroethane and one part by volume of acetic acid.

11. The process of claim 10 wherein the 1-[2,5-bis(2,2,2-trifluoroethoxy)phenyl]ethanone that is subjected to chlorination is the crude reaction product obtained by (1) reacting 1,4-dibromobenzene with 2,2,2-trifluoroethanol in the presence of cupric bromide, sodium hydride, and N,N-dimethylformamide to form a reaction mixture containing 1,4-bis(2,2,2-trifluoroethoxy)benzene, (2) extracting the reaction mixture with 1,2-dichloroethane to form a crude 1,4-bis(2,2,2-trifluoroethoxy)benzene extract, (3) washing the extract to remove N,N-dimethylformamide, and (4) acetylating the crude 1,4-bis(2,2,2-trifluoroethoxy)benzene in the presence of a Lewis acid and 1,2-dichloroethane and acidifying and washing the resultant reaction mixture to provide an organic phase comprising a crude, wet 1-[2,5-bis(2,2,2-trifluoroethoxy)phenyl]ethanone.

* * * * *